United States Patent [19]

Hill et al.

[11] 4,442,297
[45] Apr. 10, 1984

[54] MANAGANESE COMPOUNDS AND SORPTION OF GASES USING MANGANESE COMPOUNDS

[75] Inventors: William E. Hill, Auburn, Ala.; Charles A. McAuliffe, Altrincham, England

[73] Assignee: Facilitated Separations, Inc., Towson, Md.

[21] Appl. No.: 262,705

[22] Filed: May 11, 1981

Related U.S. Application Data

[63] Continuation-in-part of Ser. No. 157,028, Jun. 6, 1980, abandoned.

[51] Int. Cl.³ ............................................. C07F 13/00
[52] U.S. Cl. .................................. 549/206; 260/429 R; 549/208
[58] Field of Search .................... 260/429 R, 333, 338, 260/340.6, 343.5, 345.1, 346.11; 549/206, 208

[56] References Cited

U.S. PATENT DOCUMENTS

| | | | |
|---|---|---|---|
| 3,013,039 | 12/1961 | Lambert et al. | 260/429 R |
| 3,443,916 | 5/1969 | Rolfe | 260/429 R X |
| 3,954,821 | 5/1976 | Herskovitz et al. | 260/429 R |
| 4,251,452 | 2/1981 | McAuliffe et al. | 260/429 R |

*Primary Examiner*—Helen M. S. Sneed
*Attorney, Agent, or Firm*—Wegner & Bretschneider

[57] ABSTRACT

There are disclosed manganese compounds of the formula $$Mn^{II}LX_2(Q)_n \qquad (I)$$

wherein L is a monodentate ligand of the formula $$PR^1R^2R^3 \qquad (II)$$

wherein $R^1$, $R^2$, and $R^3$ are identical or different and are substituted or unsubstituted alkyl, cycloalkyl, alkenyl, alkynyl, or aryl; or hydrogen providing that no more than two of the $R^1$, $R^2$, and $R^3$ groups are substituted or unsubstituted aryl groups and that at least one of $R^1$, $R^2$, and $R^3$ is a substituted or unsubstituted alkyl, cycloalkyl, alkenyl, alkynyl, or aryl group, X is a species capable of existing as an anion, e.g., Cl, Br, Q is a solvento molecule capable of forming a chemical bond to the manganese, and n is 1, 2, or 3 solvent donor atoms.

The manganese compounds are useful in the separation of a gas such as oxygen, hydrogen, sulfur dioxide, an alkene, and carbon monoxide from fluids containing these gases.

18 Claims, No Drawings

MANAGANESE COMPOUNDS AND SORPTION OF GASES USING MANGANESE COMPOUNDS

REFERENCE TO RELATED APPLICATION

This is a continuation-in-part of copending application Ser. No. 157,028 filed June 6, 1980 now abandoned.

The present invention relates to manganese compounds. The present invention also relates to the sorption of gases using these manganese compounds, particularly sorption applied in the purification of gases, more particularly in the purification of nitrogen by the removal of traces of oxygen and in the production of oxygen from air. The invention also relates to adducts formed of manganese compounds and molecules of a gas.

BACKGROUND OF THE INVENTION

It is known that certain metal complexes take up gases to form adducts from which those gases can be recovered. This is true of the cobalt(II) complex known as the Salen Chelate and related Fluomine chelate complexes; in addition, those complexes of the Vaska type, in which the metal is iridium, ruthenium, osmium, or rhodium, all take up oxygen reversibly. Under moderate conditions, the adducts do not release oxygen to regenerate the sorbent complexes sufficiently readily to enable oxygen to be produced or nitrogen to be purified on a commercial scale.

Complexes have now been found that take up gases to form adducts from which the gases can be readily recovered.

GENERAL DESCRIPTION OF THE INVENTION

The present invention is directed to a compound of the formula $$Mn^{II}LX_2(Q)_n \quad (I)$$

wherein L represents a monodentate ligand of the formula $$PR^1R^2R^3 \quad (II)$$

wherein $R^1$, $R^2$, and $R^3$ are identical or different and represent substituted or unsubstituted alkyl, cycloalkyl, alkenyl, alkynyl, or aryl groups or hydrogen provided that no more than two of the groups $R^1$, $R^2$, and $R^3$ are substituted or unsubstituted aryl groups and that at least one of the groups $R^1$, $R^2$, and $R^3$ is a substituted or unsubstituted alkyl, cycloalkyl, alkenyl, alkynyl, or aryl group, X is a species capable of existing as an anion and represents —Cl, —Br, —I, —CN, —NO$_2$, —NO$_3$, —OH, —NCS, —NCSe, or —NCO, Q is a solvento molecule capable of forming a chemical bond to the manganese and is derived from, e.g., pyran, furan, tetrahydrofuran, dioxane, tetrahydropyran, diglyme, triglyme, crown ethers, polymeric ethers (e.g., Santovac), and fluorinated derivatives of these solvento molecules, and n is the number of solvent donor bonds to the manganese and is 1, 2, or 3.

The present invention is directed also to a method of separating a gas from a fluid comprising the gas wherein the fluid, which is generally gaseous itself, is treated with a compound of formula (I) so that the gas is sorbed thereby.

Although it has not been confirmed, applicants theorize that the manganese compounds of the present invention have representative formulae

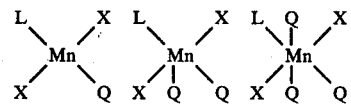

wherein L, X, and Q are as defined previously.

The configurations of course will change depending upon the value of n.

PREFERRED EMBODIMENTS OF THE INVENTION

While X may be selected from a range of atoms or groups capable of existing in anionic form, the halides (Cl, Br, and I), selenocyanate, and thiocyanate are preferred as compounds containing these anions show particularly rapid rates of oxygen uptake.

In general, it is preferred for each of the groups $R^1$, $R^2$, and $R^3$ to represent a substituted or unsubstituted alkyl, cycloalkyl, alkenyl, alkynyl, or aryl group and for at least one of the groups $R^1$, $R^2$, and $R^3$ to represent a radical of the formula —CH$_2$R$^a$ where R$^a$ represents hydrogen or a substituted or unsubstituted alkyl or cycloalkyl group. When the group R$^a$ is a substituted-alkyl group, the substituent is generally carried on a carbon atom which is spaced from phosphorus by at least two carbon atoms. The alkyl group preferably contains at least four carbon atoms and no more than ten carbon atoms in a chain. The alkyl group may be substituted by one or more aryl groups in which case it is preferable for the aryl group substituent to carry at least one electron donating substituent such as an alkyl group. The group R$^a$, when present, may be an unsubstituted alkyl or cycloalkyl group, for example a branched alkyl group. It is preferred that the group R$^a$ is a straight chain alkyl group containing at least one and no more than ten carbon atoms.

Representative $R^1$, $R^2$, and $R^3$ groups include methyl, ethyl, n-propyl, isopropyl, n-butyl, isobutyl, t-butyl, pentyl, hexyl, octyl, nonyl, decyl, dodecyl, cyclopropyl, cyclobutyl, allyl, vinyl, propargyl, phenyl, and tolyl. The $R^1$, $R^2$, and $R^3$ groups can be unsubstituted or substituted with groups such as C$_1$–C$_4$ alkyl, halogen, C$_1$–C$_4$ alkoxy, and the like.

When one or more of the groups $R^1$, $R^2$, and $R^3$ is an aryl group, the aromatic ring in the group preferably carries one or more electron donating substituent(s), typically an alkyl substituent. Other electron donating substituents can be used.

Ligands of particular interest include those of the following formulae wherein Cy represents cyclohexyl, Ph represents phenyl, Pn represents n-pentyl and R represents Me, Et, Pr$^n$, Pr$^i$, Bu$^n$, Bu$^i$, Pn, vinyl, allyl:-

PhPR$_2$, Ph$_2$PR, CyPR$_2$, Cy$_2$PR, PR$_3$, MePR$_2$, EtPR$_2$, Pr$^n$PR$_2$, Bu$^n$PR$_2$, PPh$_2$H. The ligands PMe$_3$, PEt$_3$, PPr$_3^n$, PPr$_3^i$, PBu$_3^n$, PBu$_3^i$, PEt$_2$Me, PEtMe$_2$, PPhMe$_2$, PPhEt$_2$, PPh$_2$Me, PPh$_2$Et, and PPh$_2$H are of special interest.

Compounds of formula (I) may be used to take up various gases such as oxygen, hydrogen, sulfur dioxide, alkenes (e.g. ethylene), and carbon monoxide from fluids containing one or more of the gases. As hereinbefore indicated, the compounds find particular application in the removal of trace amounts of oxygen from gases such as nitrogen and in the production of oxygen from air. For the former application, it is preferred that X be Cl, Br, or I and for the ligand L to be $L^1$ which represents $PPhMe_2$, $PPhEt_2$, $PMe_3$, $PPr_3^n$, $PPr_3^i$, $PBu_3^n$, or $PBu_3^i$. For the latter application however, it is generally preferred that X be thiocyanate or selenocyanate as compounds such as $Mn(NCS)_2Bu_3^nP(Q)_n$ and $Mn(NCSe)_2$-$Bu_3^nP(Q)_n$ can be used to sorb and desorb oxygen at pressures near ambient. When X is thiocyanate, the ligand L is preferably one of the group $L^1$. Compounds in which X represents Cl, Br, or I are also of interest for use in the production of oxygen from air and in this case it is preferred for the ligand L to be $PPh_2Me$ or $PPh_2Et$ or $PPhEt_2$ (e.g., $PPhEt_2MnBr_2(Q)_n$). The present invention allows oxygen, which is substantially free from inert gases such as nitrogen and argon, to be recovered from air.

Compounds from formula (I) may be prepared by treating an appropriate manganese(II) salt having the formula $MnX_2$ with the ligand L in a donor solvent having a molecule Q capable of forming a chemical bond to the manganese. Partial removal of the solvent yields an oil or crystalline solid which changes color on uptake of oxygen from air from a pale color to an intense green, blue, purple, or pink hue for example. Because of the reactivity of the ligand molecules towards oxygen, the ligand is in practice usually manipulated in oxygen-free conditions, for example under nitrogen. It is generally necessary for the preparation to be conducted under rigorously anhydrous conditions using starting materials which have been thoroughly dried before use. The manganese salts in particular are preferably dehydrated by prolonged heating in vacuo.

The solvent used to carry out the reaction is one that has a molecule capable of forming a chemical bond to the manganese. Representative solvents include tetrahydrofuran, dioxane, tetrahydropyran, diglyme, triglyme, crown ethers, polymeric ethers (e.g., Santovac), and any fluorinated derivatives thereof. It is important that the solvent employed be thoroughly dehydrated before use. The solvents belong to a class known as donor solvents, i.e., solvents capable of forming a bond with the manganese. Ethers, cyclic ethers, oligomeric and polymeric ethers and their perfluorinated derivatives are particularly suitable. It is important to note that for those purposes when the manganese compounds are to be used in solution, the manganese compounds can be prepared in situ in the solvent of choice by merely mixing the $MnX_2$ salt and the ligand L in the solvent and stirring.

It is highly desirable that the method of separating the gas from the fluid be operated under strictly anhydrous conditions so that the risk of decomposition of the compound is minimized.

Although many of the present compounds are remarkably robust and withstand a great number of sorption-desorption cycles without decomposition, it is preferable, at least for certain compounds, that the amount of gas, for example, oxygen, available to the compounds is controlled in order to reduce the risk of irreversible deactivation thereof.

In practice, the present compounds are employed in solution or are distributed on the surface of a support material, for example, a mass of glass beads, during contact with the gas-containing fluid, which fluid is typically itself gaseous, so that the surface area accessible to the fluid is relatively increased.

Gases are in general conveniently removable from fluids containing same with the present compounds by adjustment of the external pressure or temperature. In a typical system suitable for the production of oxygen from air, a mass of particulate support material carrying the active compound, e.g. a bed thereof, in a container provided with an inlet for fluid, is treated with pressurized fluid containing oxygen. Oxygen is removed from the fluid by the compound, the residual fluid is separated from the support material carrying the active compound, and oxygen is recovered therefrom by a relative reduction in pressure or a relative increase in temperature. The cycle may then be repeated with the deoxygenated compound and more pressurized fluid containing oxygen. Alternatively, a solution containing the active compound may be pressurized and pumped into a vessel packed with a particulate material through which a gaseous fluid containing oxygen, such as air, is passed under pressure preferably in counter-current flow thereto. Oxygen transfers from the fluid to this solution which then passes into a chamber in which the pressure is relatively decreased, for example, to atmospheric. Oxygen boils out and may be recovered and the residual solution is used in further repetitions of the cycle.

In general as the temperature of the sorbent compound is lowered, the capacity thereof for gas increases but the rate of desorption decreases. Operating temperatures usually reflect a compromise between these factors but for guidance temperatures generally are in the range of $-50°$ C. to $+40°$ C.

The present invention also includes within its scope an adduct of a gas with a compound of formula (I), from which adduct the latter compounds may be regenerated by removal of the gas, e.g., by reduction in pressure or increase in temperature. Such compounds are considered to have the formula $MnLX_2(Q)_mY$, wherein Y represents one or more molecules of a gas such as $H_2$, $SO_2$, CO or an alkene, e.g. ethylene, or one molecule of oxygen, m is one or two, and L, X, and Q as previously defined.

The following examples are representative of methods of how to make and how to use the compounds (solvento complexes) of the present invention. For all examples, the ESR data was obtained on a Varian E9 Spectrometer operating at 9.5 GHz in solvent glasses at $-186°$ C.

The complexes were made by reacting an $MnLX_2$ compound (prepared in a manner similar to the preparation of the compounds in U.S. Pat. No. 4,251,452 to McAuliffe et al.) with a solvento-compound, e.g. tetrahydrofuran and diglyme. The complexes can be prepared by the direct reaction of the $MnLX_2$ compound with the solvento-compound or the complexes can be prepared in situ by reacting an $MnX_2$ salt, a ligand (L), and the solvento-compound.

EXAMPLE I

In this example, the following $MnLX_2$-solvento complexes wherein the solvento group is supplied by tetrahydrofuran[1] were prepared (the observed spectra, X-band, kG is reported also):

| Complex | Observed Spectra, X-band, kG. |
|---|---|
| $Mn(PPhMe_2)I_2$ | 1.25(m), 323(s), 5.4(w), 7.9(m) |
| $Mn(PPr_3^n)I_2$ | 1.25(s), 3.35(m), 5.5(m), 8.0(m) |
| $Mn(PPhMe_2)Br_2$ | 1.38(s), 3.25(m), 5.3(w), 7.5(w) |

-continued

| Complex | Observed Spectra, X-band, kG. |
|---|---|
| $Mn(PBu_3^n)Br_2$ | 1.2(s), 3.35(m), 5.6(w), 7.9(m) |
| $Mn(PPhMe_2)Br_2$ | 1.38(s), 3.25(m), 5.3(w), 7.5(w) |
| $Mn(PPr_3^n)Br_2$ | 1.25(s), 3.35(m), 5.5(m), 8.00(m) |
| $Mn(PPhMe_2)Cl_2$ | 1.0(w), 1.55(vw), 3.35(s), 5.3(vvw) |
| $Mn(PBu_3^n)Cl_2$ | 1.1(w), 1.7(m), 3.35(s), 5.4(w) |
| $Mn[P(allyl)_3]Cl_2$[2] | 1.0(vw), 1.9(w), 3.23(s), 5.3(vw) |

[1]Distortion parameters have values in range of D ≃ 0.1 and λ<0.1
[2]Hyperfine splitting for 3.23(s) peak, six lines, with a splitting of 94 gauss.

EXAMPLE 2

This example reports the preparation and ESR spectra for the solvento complexes formed of the $MnLX_2$ complex and solvento group supplier listed below:

| Complex | Solvent | Observed Spectra, X-band(kG.)[3] |
|---|---|---|
| $Mn(PPhMe_2)I_2$ | tetrahydrofuran | 1.25(m), 3.23(s), 5.4(w), 7.9(m) |
| $Mn(PPhMe_2)I_2$ | diglyme[4] | 1.55(s), 3.30(m), 5.5(w), 8.0(vw) |
| $Mn(PPhMe_2)Br_2$ | tetrahydrofuran | 1.38(s), 3.25(M), 5.3(w), 7.5(w) |
| $Mn(PPhMe_2)Br_2$ | diglyme[5] | 1.6(s), 3.25(m), 5.3(w), 8.1(vw) |
| $Mn[P(allyl)_3]Cl_2$ | tetrahydrofuran | 1.0(vw), 1.9(w), 3.23(s), 5.3(vw) |
| $Mn[P(allyl)_3]Cl_2$ | diglyme | 0.9(m), 1.6(s), 3.25(s), 5.2(w) |

[3]Distortion parameters D ≃ 0.1, λ<0.1 for all complexes
[4]Fine structure shows six lines at 3.30 (A = 89 gauss average) and multiple lines at 1.55 from which six lines can be seen with (A ≃ 89 gauss).
[5]Complex resonance at 1.6 but observable are six lines (A ≃ 94 gauss).

The following complexes were prepared in toluene (a non-coordinating solvent) for comparative and discussion purposes:

| Complex | X-band Observed Spectra, KG | g |
|---|---|---|
| $Mn(PPhMe_2)I_2$ | 3.219(s) | 2.01 |
| $Mn(PPhMe_2)Br_2$ | 3.250(s) | 2.00 |
| $Mn(PPhMe_2)Cl_2$ | 3.30(s) | 2.00 |
| $Mn[P(allyl)_3]Cl_2$ | 3.32(s) | 2.00 |
| $Mn(PPhMe_2)(NCS)_2$ | 3.23(s) | 2.00 |

A comparison of the ESR data of the solvento complexes made in accordance with the present invention to the complexes in toluene (non-solvento: a non-coordinating solvent) shows a striking difference between those complexes. For the $[MnLX_2]_x$ complexes in toluene only a broad resonance at g≃2 is observed in all cases. The width of this line varies from 600>663 gauss for all of the complexes $[Mn(PPhMe_2)X_2]_x$ (X=Cl, Br, I) and $[Mn[P(allyl)_3]Cl_2]_x$. A single resonance for $[Mn(PPhMe_2) (NCS)_2]_x$ is also observed through much more narrow (≃250 gauss). Any compound with regular cubic symmetry such as $MnL_4$ or $MnL_6$ will give a single line at g=2. However it has been pointed out by Dowsing and Gibson that manganese complexes which cannot have a regular structure (such as $[MnLX_2.sol-vento]$) can give a single resonance at g≃2 when the complexes are polymeric.[6] Thus, it is concluded that the complexes $[MnLX_2]_x$ in toluene are polymeric with the single g≃2 resonance arising from magnetic interaction of the close proximity neighboring manganese ions.
[6]R. D. Dowsing, J. F. Gibson, D. M. L. Goodgame, M. Goodgame, P. J. Hayward, Nature, 219, 1037 (1968).

The solvento spectra are similar to those observed for manganese complexes of the type $[MnL_2X_2]$ or $[MnL_4X_2]$ in either a tetrahedral or octahedral geometry.[7,8,9] Distortion parameters D and λ obtained from the esr spectra fall in the range D≃0.1,λ<0.1 indicating distortion from regular symmetry (as expected for [$MnLX_2$.solvento] complexes). In view of molecular weight studies reported infra, it is shown that the complexes are monomeric in the coordinating solvent. Thus the complexes in coordinating solvent most likely are pseudo octahedral $[MnLX_2(S)_3]$ [S=solvento donor atoms] or pseudo tetrahedral $[MnLX_2(S)]$.
[7]R. D. Dowsing and J. F. Gibson, J. Chem. Phys., 50, 294 (1969).
[8]R. D. Dowsing, J. F. Gibson, D. M. L. Goodgame, M. Goodgame, and P. J. Hayward, J. Chem. Soc. (A), 1242 (1969).
[9]D. M. L. Goodgame, M. Goodgame, and P. J. Hayward, J. Chem. Soc., (A), 1352 (1970)

In all cases where hyperfine coupling constants (A) could be observed, the values were in the range of 75 to 95 gauss. This is a typical value for octahedral hyperfine interactions (indicating octahedral geometry for the complex—hence $MnLX_2(S)_3$). Values for tetrahedral hyperfine interactions are in the range 40 to 65 gauss.[10]
[10]B. R. McGarvey, Transition Metal Chemistry, Vol 3, 89, (1966).

Molecular Weight Measurements

Molecular weight measurements were performed on a Chromatix KMX-16 laser differential refractometer. These measurements employ a laser-light scattering technique which determines the molecular weight via measurement of specific refractive index increments by high precision laser differential refractometry. Prior to measurements on the KMX-16, some parameters must be determined by measurement of the solution on a conventional differential refractometer.

Specific measurements were concentrated on $Mn(PBu_3^n)I_2$ in THF since this species does not bind oxygen at ambient temperature under $O_2$ pressures of 1 atm. or less. Also, ESR studies showed that $Mn(PR_3)I_2$ in THF was most likely octahedral as discussed supra. Furthermore, the monomeric molecular weight of the complex was quite high (511 gms/mole) leading to greater accuracy in the determination.

Results of two independent determinations were 588 gms/mole and 546 gms/mole (calculated 511 gms/mole) indicating that the complex is monomeric in tetrahydrofuran in the deoxygenated case. Clearly the experimental molecular weights will not reflect the coordinated THF since most likely coordinated THF is rapidly exchanging with free THF at room temperature. In any event bound solvent will not be shown by this technique. Thus, the results of the ESR measurements coupled with the mw measurements clearly show the presence of a species

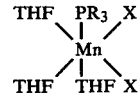

It is reasonable to assume that other complexes adopt a similar geometry in THF.

Elemental Analyses

Elemental analyses of the complexes prepared in toluene, benzene, or dichloromethane clearly show the general formula $MnLX_2$ reported by McAuliffe.[11] However, isolation of complexes from THF and diglyme give analyses that clearly indicate the presence of solvent although the precise stoichiometry is variable depending on the method of isolation or the length of time the complexes are left under high vacuum. In general the longer the evacuation time the closer the complex analyzes to $MnLX_2$. Thus, the elemental analyses suggest that the solvent is very loosely bound and can be removed in vacuo. Therefore, it is not surprising that complexes of the exact analysis of, e.g., $MnLX_2(THF)_3$ have not been obtained.

[11] C. A. McAuliffe, H. Al-Khateeb, M. H. Jones, W. Levason, K. Minten, and F. P. McCullough, *J. Chem. Soc. Chem. Comm.*, 736 (1979).

EXAMPLE 3

The following example reports the infrared spectra of various solvento complexes of the present invention. The infrared spectra were obtained on a Perkin Elmer 580 Spectrophotometer in nujol and Fluorolube mulls.

A series of $MnLX_2$ complexes were produced and analyzed. Once obtained these complexes were dissolved in THF and the resulting mixture was allowed to stir for 24 hours. Thereafter, any remaining solvent was removed in vacuo.

The process of obtaining a solid product appears to proceed in two stages: initially the mixture, once all free solvent is evaporated, leaves an oily semi-solid. In the second stage the semi-solid is allowed to stand for 24–48 hours in which time this mixture becomes a solid.

The solid products in general are white for the chloride and bromide, light pink/orange for an iodide, and yellow for a thiocyanate.

Ths most widely studied solvent was tetrahydrofuran (THF) and coordination to a complex of the type $MnLX_2$ enhances the oxygen binding ability of the complex. The most extreme example is believed to be $Mn(PPhMe_2)Cl_2$. This complex in the solid form is not $O_2$ active; in contrast any coordination of THF produces a species which rapidly binds oxygen to give a deep purple solid from the normal white colors.

Infra-red measurements on both $MnLX^2$, unsolvated complexes and $[MnLX_2(THF)_x]$ complexes were conducted. For $MnLX_2$, prepared by the reaction of the $MnX_2$ salt with the phosphine in toluene, benzene or dichloromethane (all non-coordinating solvents), no solvent bands were observed. Table 1 lists the results of the preparation of $[MnLX_2(THF)_x]$ complexes and clearly solvent bands are observed. Furthermore, comparison with the infrared spectra of known manganese-tetrahydrofuran complexes show coordinated tetrahydrofuran.

of the non-coordinating solvent such as toluene or 1,2,-dichloroethane, no such restrictions apply to the binding site and the $O_2$ ligand can move smoothly into the vacant binding site.

This arrangement in a coordinating solution is different from that in a solvent such a toluene. This can be expressed as:

| $MnLX_2$ | $MnLX_2(S)n$ | |
|---|---|---|
| non-coordinating | coordinating | S = Solvent |

EXAMPLE 4

This example reports the results of dioxygen uptake by $MnLX_2.(Solvento)_x$ complexes.

Dioxygen uptake was measured by using a gas burette. In all cases true solutions of the complexes were used. Solutions were made either by dissolving the solid complex in the solvent or by "in situ" mixing of equimolar amounts of the phosphine ligand (L), and the anhydrous salt, $(MnX_2)$ in the solvent. The measurements with the "in situ" preparations were carried out after 20 hours to insure complex formation.

The complexes investigated were of the formula $MnLX_2.(Solvento)_x$ with $L=PR'_2R''$, $PR_3$; $RLR=$alkyl; $X=Cl$, Br, I, NCS; and solvent=ether solvents. Uptakes were measured at room temperature (25° to 28° C.) and/or at $-78°$ C. $[CO_{2(s)}$bath) and/or 0° C. (Ice bath). Atmospheric pressure of $O_{2(g)}$ was maintained constantly over the solution.

Dioxygen uptake by all solvents and solutions were made under the same conditions. Solvent uptakes were subtracted from the quantity of dioxygen adsorbed by the complex solution in order to determine the amount of $O_2$ uptaken by the complex alone. Solution uptakes were followed up to two hours at a time. Dioxygen uptakes. The representative solvents used were tetrahydrofuran (THF) and diglyme. The table shows the solvent uptake at various temperatures at an oxygen partial pressure of 1 atm.

TABLE 1

| THF[12] | | | $MnLX_2(THF)_x$ | | | | |
|---|---|---|---|---|---|---|---|
| (S) | THF[12][13] | $Mn(THF)_6(SbCl_6)_2$[12] | Cl | Br | I | NCS | Assignment |
| 1241 s | 1238 m | 1246 m | — | 1235 ms | 1247 w | 1235 W | $CH_2$ wag |
| 1179 vs | 1182 s | 1179 s | 1170 s | 1182 ms | 1150 s | 1180 m | $\nu$ ring |
| 1058 vs | 1069 vs | 1037 whs | 1042 wsh | — | 1042 wsh | — | $\nu$ ring |
| 1043 vs | 1030 msh | 1018 vs | 1030 vs | 1030 vs | 1030 vs | 1035 vs | $\rho CH_2$ |
| 954 s | — | 960 w | 960 vw | 980 m | 960 m | 960 m | $\nu$ cc/c-o |
| 921 s | | | | | | | |
| 908 s | 910 vs | 920 m | 922 m | — | 910 m | 910 m | ring breathing |
| 891 s | | | | | | | |
| 871 s | | 859 vs | 875 vs | 870 vs | 875 vs | 875 vs | $\rho CH_2$ |
| 838 vs | | 843 wsh | — | 845 wsh | 845 wsh | 840 wsh | $\rho CH_2$ |
| 662 (s) | 658 (s) | 673 m | 680 w | 670 w | 690 s | 675 w | $\delta$ ring in plane |

[12] W. L. Driessen and M. Heijer, *Inorg. Chim. Acta*, 33, 261 (1979).
[13] Peaks due only to the presence of THF shown.

Isotherm Studies

It has been found empirically that the affinity towards $O_2$ of a given complex is higher in toluene than in THF. If one considers the isotherm of $Mn(PBu_3)I_2$ with $O_2$ this becomes immediately obvious in a quantative form.

The explanation for this behavior in solution is that the solvent is somewhat coordinated to the metal center and is blocking the $O_2$ binding site. However, in the case

TABLE 2

| Solvent[a] | Temperature (0° C.) | Millimoles $O_{2(g)}$ |
|---|---|---|
| THF | R.T. | 0.86 |
| | 0° | 0.93 |
| | −78° | 1.0 |
| Diglyme | R.T. | 0.61 |
| | 0° | 0.68 |

TABLE 2-continued

| Solvent[a] | Temperature (0° C.) | Millimoles $O_{2(g)}$ |
|---|---|---|
| | −78° | 1.20 |

[a] volumes of 100 ml

The dioxygen uptakes of the complex solutions are shown in the following tables. The percent oxygenation is calculated as [millimoles $O_2$ uptaken by complex/millimoles complex]×100. The color change upon oxygenation is also indicated in those tables.

TABLE 3

Dioxygen uptake of representative complexes of the type $Mn[PR_3]X_2 \cdot (Solvento)_x$ [R = alkyl] in Ether-Function Solvents.

| $Mn[PR_3]X_2$ PR$_3$ | X | Solvent | Temperature | % Oxygenation | Color |
|---|---|---|---|---|---|
| PBu$_3^n$ | I | THF | −78° | 93 | Colorless - dark green |
| PBu$_3^n$ | I | THF | R.T. | 38 | Colorless - dark green |
| PBu$_3^n$ | Br | THF | −78° | 55 | Colorless - dark blue |
| PBu$_3^n$ | Br | THF | 0° | 60 | Colorless - dark blue |
| PBu$_3^n$ | Br | Diglyme | −78° | 23 | White - dark red |
| PBu$_3^n$ | Br | Diglyme | −0° | 16 | White - deep violet |
| PBu$_3^n$ | NCS | Diglyme | −78° | 0.3 | No change observed |
| PBu$_3^n$ | NCS | Diglyme | 0° | 5.2 | Pale yellow - brown orange |
| PBu$_3^n$ | NCS | Diglyme | R.T. | 8.0 | Pale yellow - brown orange |
| PPent$_3^n$ | I | THF | −78° | 92 | Colorless - deep purple |
| PPent$_3^n$ | Br | THF | −78° | 91 | Colorless - blue |
| PPent$_3^n$ | Cl | THF | −78° | 76 | Colorless - red |

TABLE 4

Dioxygen uptake of representative complexes of the type $Mn[PR'_2R'']X_2 \cdot (Solvento)$ [R' = alkyl; R'' = aryl] in ether-function solvents

| $Mn[PR'_2R'']X_2$ PR'$_2$R'' | X | Solvent | Temperature | % Oxygenation | Color |
|---|---|---|---|---|---|
| PMe$_2$(C$_6$H$_5$) | I | THF | −78° | 100 | Colorless - dark green |
| PMe$_2$(C$_6$H$_5$) | I | THF | 0° | 65 | Colorless - green |
| PMe$_2$(C$_6$H$_5$) | I | Diglyme | −78° | 30 | Colorless - dark green |
| PMe$_2$(C$_6$H$_5$) | I | Diglyme | 0° | 18 | Colorless - green |
| PMe$_2$(C$_6$H$_5$) | I | THF | −78° | 65 | Colorless - deep violet |
| PMe$_2$(C$_6$H$_5$) | Br | Diglyme | −78° | 12 | Colorless - deep violet |
| PMe$_2$(C$_6$H$_5$) | Br | Diglyme | 0° | 11 | Colorless - deep violet |
| PMe$_2$(C$_6$H$_5$) | Cl | Diglyme | −78° | <1 | Colorless - pale pink |
| PMe$_2$(C$_6$H$_5$) | Cl | Diglyme | 0° | <1 | No change observed |
| PMe$_2$(C$_6$H$_5$) | NCS | Diglyme | 0° | <1 | No change observed |

General Observations

A. All the complexes MnLX$_2$·(solvento) with L=PR'$_2$R'', PR$_3$ [R:R=alkyl; R''=aryl] and X=Cl, Br, I, NCS, uptake dioxygen in ethers.

B. The solution uptake of $O_2$ is reversible. The complexes can undergo several (over 5, depending on temperature) oxygenation - deoxygenation cycles, before showing considerable deterioration.

C. The affinity for dioxygen is affected by solvent, temperature, and the nature of the ligands. Some general trends are:

1. Affinity decreases in the series I>Br>Cl and dependent on solvent environment, NCS can be more or less effective than Cl.
2. Affinity is higher for the trialkyl phosphines than for aryl substituted phosphines PBu$_3^n$∼PPentyl$_3$>PMe$_2$(C$_6$H$_5$)>PPh$_2$Me
3. Affinity is higher at low temperatures: −78° C.>0° C.>R. T. However, for X=NCS the situation is reversed.

D. Rate of oxygenation was followed in several cases. The trends of rate follow in general, the trends of affinity. The rate of uptake increases with the pressure of $O_{2(g)}$ over the solution and the concentration of the complex.

What is claimed is:

1. A compound of the formula $$Mn^{II}LX_2(Q)_n \qquad (I)$$

wherein L represents a monodentate ligand of the formula $$PR^1R^2R^3 \qquad (II)$$

wherein

R$^1$, R$^2$, and R$^3$ are identical or different and represent alkyl, cycloalkyl, alkenyl, alkynyl, or aryl groups or hydrogen with the proviso that no more than two of R$^1$, R$^2$, and R$^3$ are aryl groups and that at least one of R$^1$, R$^2$, and R$^3$ is a alkyl, cycloalkyl, alkenyl, alkynyl, or aryl group, X is a species capable of existing as an anion and is selected from the group consisting of Cl, Br, I, CN, NO$_2$, NO$_3$, OH, NCS, NCSe, and NCO, Q is a solvento molecule that forms a chemical bond to the manganese, and n is the number of solvent donor bonds to the manganese and is 1, 2, or 3.

2. The compound of claim 1 wherein the solvento molecule Q is derived from a compound selected from the group consisting of pyran, furan, tetrahydrofuran, dioxane, tetrahydropyran, diglyme, triglyme, crown ethers, polymeric ethers, and fluorinated derivatives thereof.

3. The compound of claim 1 wherein X is selected from the group consisting of Cl, Br, I, NCS, and NCSe.

4. The compound of claim 1 wherein none of R$^1$, R$^2$, and R$^3$ is hydrogen.

5. The compound of claim 1 wherein at least one of $R^1$, $R^2$, and $R^3$ is a radical of the formula $-CH_2R^a$ wherein $R^a$ is selected from the group consisting of hydrogen, alkyl, cycloalkyl, alkenyl, and alkynyl.

6. The compound of claim 5 wherein $R^a$ is a straight chain alkyl, alkenyl, or alkynyl group having no more than 10 carbon atoms.

7. The compound of claim 1 wherein L represents $PhPR_2$, $CyPR_2$, $Ph_2PR$, $Cy_2PR$, $PR_3$, $MePR_2$, $EtPR_2$, $Pr^nPR_2$, $Bu^nPR_2$, or $PPh_2H$ where Cy is cyclohexyl, and R is any of Me, Et, Prn, $Pr^i$, $Bu^n$, $Bu^i$, Pn (representing n-pentyl), allyl, or vinyl.

8. The compound of claim 7 wherein L is selected from the group consisting of $PMe_3$, $PEt_3$, $PPR_3^n$, $PPR_3^i$, $PBu_3^n$, $PBu_3^i$, $PEt_2Me$, $PEtMe_2$, $PPhMe_2$, $PPhEt_2$, $PPh_2Me$, and $PPh_2Et$.

9. The compound of claim 8 selected from the group consisting of $MnPMe_3X_2(Q)_n$, $MnPEt_3X_2(Q)_n$, $MnPPr_3^nX_2(Q)_n$, $MnPPr_3^iX_2(Q)_n$, $MnPBu_3^nX_2(Q)_n$, $MnPMe_2PhX_2(Q)_n$, and $MnPEt_2PhX_2(Q)_n$ wherein X is selected from the group consisting of Cl, Br, and I.

10. The compound of claim 8 of the formula $MnPBu_3^n(NCS)_2(Q)_n$.

11. The compound of claim 1 wherein $MnLX_2$ is a member selected from the group consisting of $Mn(PPhMe_2)I_2$, $Mn(PPr_3)I_2^n$, $Mn(PPhMe_2)Br_2$, $Mn(PBu_3)Br_2$, $Mn(PPhMe_2)Br_2$, $Mn(PPr_3)Br_2^n$, $Mn(PPhMe_2)Cl_2$ and $Mn[P(allyl)_3]Cl_2$ and Q is supplied by tetrahydrofuran.

12. The compound of claim 1 wherein the $MnLX_2$ complex and the solvento group suppliers are

| Complex | Solvento group supplier |
|---|---|
| $Mn(PPhMe_2)I_2$ | tetrahydrofuran |
| $Mn(PPhMe_2)I_2$ | diglyme |
| $Mn(PPhMe_2)Br_2$ | tetrahydrofuran |
| $Mn(PPhMe_2)Br_2$ | diglyme |
| $Mn[P(allyl)_3]Cl_2$ | tetrahydrofuran |
| $Mn[P(allyl)_3]Cl_2$ | diglyme |

13. An adduct of the formula $$MnLX_2Q_mY \qquad (III)$$

wherein

L represents a monodentate ligand of the formula $$PR^1R^2R^3 \qquad (II)$$

wherein $R^2$, $R^2$, and $R^3$ may be identical or different and represent alkyl, cycloalkyl, alkenyl, alkynyl, or aryl groups or hydrogen with the proviso that no more than two of $R^1$, $R^2$, and $R^3$ are aryl groups and that at least one of the groups $R^1$, $R^2$, and $R^3$ is a alkyl, cycloalkyl, alkenyl, alkynyl, or aryl group, X is a species capable of existing as an anion and represents Cl, Br, I, CN, $NO_2$, $NO_3$, OH, NCS, NCSe, or NCO, Q is a solvento molecule that forms a chemical bond to the manganese, m is 1 or 2 solvento donor atoms, and Y is at least one molecule of a gas.

14. The adduct of claim 13 wherein the gas is selected from the group consisting of $H_2$, $SO_2$, CO, and an alkene.

15. The adduct of claim 13 wherein Y represents one molecule of oxygen.

16. The adduct of claim 13 wherein Q is derived from pyran, furan, tetrahydrofuran, dioxane, tetrahydropyran, diglyme, triglyme, crown ethers, polymeric ethers, and fluorinated derivatives thereof.

17. The compound of claim 1 wherein at least one of the $R^1$, $R^2$, and $R^3$ groups is substituted with a member selected from the group consisting of $C_1$–$C_4$ alkyl, halogen, and $C_1$–$C_4$ alkoxy.

18. The adduct of claim 13 wherein at least one of the $R^1$, $R^2$, and $R^3$ groups is substituted with a member selected from the group consisting of $C_1$–$C_4$ alkyl, halogen, and $C_1$–$C_4$ alkoxy.

* * * * *